(12) United States Patent
Wolicki

(10) Patent No.: US 8,137,711 B2
(45) Date of Patent: Mar. 20, 2012

(54) METHODS OF TREATING NEUROPATHY

(75) Inventor: Richard Wolicki, Imperial Beach, CA (US)

(73) Assignee: Taraxos Inc., San Diego, CA (US)

( * ) Notice: Subject to any disclaimer, the term of this patent is extended or adjusted under 35 U.S.C. 154(b) by 171 days.

(21) Appl. No.: 12/749,183

(22) Filed: Mar. 29, 2010

(65) Prior Publication Data
US 2010/0184817 A1 Jul. 22, 2010

Related U.S. Application Data

(63) Continuation of application No. 10/307,509, filed on Nov. 25, 2002, now Pat. No. 7,687,080.

(51) Int. Cl.
*A61K 36/00* (2006.01)
(52) U.S. Cl. ........................................ 424/725
(58) Field of Classification Search .................. None
See application file for complete search history.

(56) References Cited

U.S. PATENT DOCUMENTS

| 6,147,102 | A | 11/2000 | Borgman |
| 6,166,085 | A | 12/2000 | Chaplan et al. |
| 6,290,986 | B1 | 9/2001 | Murdock et al. |
| 6,376,530 | B1 | 4/2002 | Claiborne et al. |
| 6,596,900 | B2 | 7/2003 | Blakemore et al. |
| 6,689,399 | B1 | 2/2004 | Dickson |
| 6,730,667 | B2 | 5/2004 | Deagle |
| 6,770,661 | B2 | 8/2004 | Shao et al. |
| 2002/0028789 | A1 | 3/2002 | Ford |
| 2007/0225257 | A1 | 9/2007 | Baudy et al. |

OTHER PUBLICATIONS

International Search Report and Written Opinion for International Application No. PCT/US2009/058446 filed Nov. 20, 2009.
S Felby et al; NMDA receptor blockade in chronic neuropathic pain: a comparison of ketakmein and magnesim chloride; Pain, 64 (1995) pp. 283-291.
Torhild Warncke et al; Ketamine, an NMDA receptor antagonist, suppresses spatial and temporal properties of burn-induced secondary hyperalgesia in man: a double blind, cross-over comparison with morphine and placebo; Pain, 72 (1997); pp. 99-106.
Mariela Padilla et al; Topical medications for orofacial neuropathic pain: a review; JADA, vol. 131, Feb. 2000; pp. 184-195.
Marty'S Algorithm for Chronic Neuropathy, Sep. 1999, Modified Mar. 2000.
DW ACe 1998-94827, Sep. 1998, Edeburn et al.

*Primary Examiner* — Melenie McCormick
*Assistant Examiner* — Randall Winston
(74) *Attorney, Agent, or Firm* — Knobbe, Martens, Olson & Bear LLP

(57) ABSTRACT

Methods and compositions for the topical or transdermal treatment of neuropathy. More particularly, transdermal or topical compositions including a combination of ingredients that provide a surprising degree of effective relief from the symptoms of peripheral neuropathy and methods for administering the compositions to treat various neuropathies.

20 Claims, No Drawings

METHODS OF TREATING NEUROPATHY

CROSS-REFERENCE TO RELATED APPLICATIONS

This application is a continuation of U.S. application Ser. No. 10/307,509, filed Nov. 25, 2002, now U.S. Pat. No. 7,687,080. The disclosure of the above application is hereby incorporated by reference in its entirety.

BACKGROUND OF THE INVENTION

1. Field of the Invention

The present invention relates to methods and compositions for the topical treatment of neuropathy. More particularly, the present invention relates to transdermal compositions including a combination of ingredients that provide a surprising degree of effective relief from the symptoms of neuropathy and to methods for administering topical compositions to treat neuropathy.

2. Description of the Prior Art

Peripheral neuropathy is a condition involving nerve-end damage anywhere in the body. Peripheral neuropathy generally refers to a disorder that affects the peripheral nerves, most often manifested as one or a combination of motor, sensory, sensorimotor, or autonomic neural dysfunction. The wide variety of morphologies exhibited by peripheral neuropathies can each be uniquely attributed to an equally wide variety of causes. For instance, peripheral neuropathies can be genetically acquired, can result from a systemic disease, can manifest as a post-surgical complication, or can be induced by a toxic agent. Some toxic agents that cause neurotoxicities are therapeutic drugs, antineoplastic agents, contaminants in foods or medicinals, and environmental and industrial pollutants.

Neuropathy is a major complication of diabetes mellitus. No well-established treatments exist for either its symptomatic treatment or for prevention of progressive decline in nerve function. Estimates of the prevalence of neuropathy in diabetes vary widely, from a low of 5% to a high of 80%, largely due to the numerous definitions and clinical descriptions of neuropathy. Nevertheless, the additive effects of neuropathy in the suffering diabetic patient are well known and documented. The effect of the neuropathy is complex. The loss of sensory information from the foot is related to abnormal and prolonged pressure on the areas of the foot (sensory neuropathy). Motor neuropathy leads to deformity, further increasing pressure loading on the foot. In autonomic neuropathy, loss of innervation of the sweat glands results in dry skin that cracks creating an environment amenable to infection. Autonomic dysfunction contributes further by altering the distribution of micro-circulatory blood flow, directing the blood flow through shunts and away from the nutritive skin capillaries. These factors as a whole, in conjunction with foot trauma, result in skin breakdown and ulcers.

Scientists have not yet determined the mechanism that leads to nerve damage in diabetes, but it is believed to be multifactorial. These factors include genetic predisposition, metabolic and vascular abnormalities, and lack of perturbation of growth factors. The response of the peripheral nervous system to the metabolic effects of diabetes does not appear to differ between type 1 and type 2 diabetes, which suggests a likelihood of similar clinical response to therapies in the two primary forms of the disease. There seem to be a number of susceptibility factors, as yet unknown, for the development of neuropathy, which operate in the presence of hyperglycemia (high blood sugar).

Although a number of neuropathies are related to the disease diabetes mellitus, others, although not known to be related to diabetes are similar in their physiological effects on the peripheral vascular system. Such diseases include Raynaud's Phenomenon, including CREST syndrome, autoimmune diseases such as erythromatosis, and rheumatoid diseases. Other peripheral neuropathies include the following: HIV associated neuropathy; $B_{12}$-deficiency associated neuropathy; cranial nerve palsies; drug-induced neuropathy; industrial neuropathy; lymphomatous neuropathy; myelomatous neuropathy; multi-focal motor neuropathy; chronic idiopathic sensory neuropathy; carcinomatous neuropathy; acute pain autonomic neuropathy; alcoholic neuropathy; compressive neuropathy; vasculitic/ischaemic neuropathy; mono- and poly-neuropathies.

For example, among the most important toxic agents causing peripheral neuropathy are therapeutic agents, particularly those used for the treatment of neoplastic disease. In certain cases, peripheral neuropathy is a major complication of cancer treatment and is the main factor limiting the dosage of chemotherapeutic agents that can be administered to a patient (Macdonald, Neurologic Clinics 9:955-967 (1991)). This is true for the commonly administered agents cisplatin, paclitaxel and vincristine (Broun, et al., Am. J. Clin. Oncol. 16:18-21 (1993); Macdonald, Neurologic Clinics 9:955-967 (1991); Casey, et al., Brain 96:69-86 (1973)). The identification of methods for preventing or alleviating dose-limiting peripheral neuropathologic side effects would allow higher, and more therapeutically effective doses of these chemotherapeutics to be administered to patients, i.e., the therapeutic efficacy of such chemotherapeutics is typically a function of dose and therefore, increasing dosage provides increased patient survival (Macdonald, Neurologic Clinics 9:955-967 (1991); Oxols, Seminars in Oncology 16, suppl. 6:22-30 (1989)).

Tragically there is no existing method for adequately, predictably and specifically treating established neuropathic pain (Woolf C. et al., Neuropathic Pain: Aetiology, Symptoms, Mechanisms, and Management, Lancet 1999; 353: 1959-64). Present treatment methods for neuropathic pain consists of merely trying to help the patient cope through psychological or occupational therapy, rather than by reducing or eliminating the pain experienced.

Currently, there are a limited number of drugs available for the treatment of neuropathy. Most treatments composition and methods are directed towards relief of pain. Currently, there are several categories of treatments utilized, including medical procedures and drugs, which are provided locally or systemically. For example, current methods to treat neuropathic pain include administration of local anesthetic blocks targeted to trigger points, peripheral nerves, plexi, dorsal roots, and to the sympathetic nervous system. However, these treatments have only short-lived antinociceptive effects. Additionally, longer lasting analgesic treatment methods, such as blocks by phenol injection or cryotherapy raise a considerable risk of irreversible functional impairment. Furthermore, chronic epidural or intrathecal (collectively called "intraspinal") administration of drugs such as steroids, opioids or midazolam have significant side effects and questionable efficacy. Medical procedures are ineffective and often expensive, leading to various pains that many times supercede the original pain.

The current standard of practice for the non-invasive treatment of the various neuropathies include the following drug classes: (1) The Non-Steroidal Anti-inflammatory Drugs (NSAIDs); (2) Narcotic analgesics; (3) Tricyclic antidepressants; and (4) Anticonvulsants, e.g., carbamazepine and gabapentin. These classes are available commercially as oral products and, generally, are administered via the oral route. Because they are distributed systemically throughout the body, their various side effects limit their effectiveness. The NSAIDs, for example, when taken orally cause gastric distress—including ulcers. The other three classes share other common side effects, including drowsiness, dizziness, disorientation, and gastrointestinal upset to name but a few.

Several topical agents (creams, ointments, liniments and the like) have been utilized for the relief of the pains and aches of neuropathies. Most of these have provided a little, but only temporary, relief to persons suffering from pain. Many combinations of varying ointments, creams, aqueous solutions, liniments and the like for the treatment of neuropathies have been employed. The most efficacious of these contains as its active ingredient the vegetable products derived from the seed and pods of the capsicum plant, commonly known as red pepper. Capsicum-derived ointment is devised for external application to the affected area of the body by applying to the area adjacent to the muscle, joint or tendon and rubbing it into the skin. The active ingredient is capsaicin. With initial as well as persistent application, capsaicin is effective to relieve the aches and pains of various muscle or skeletal origin, such as arthritis, muscle strains, tendonitis, bursitis and soft tissue diseases.

U.S. Pat. No. 5,665,360 (Mann) relates to the treatment of peripheral neuropathies associated with diabetes mellitus by periodic topical application of a composition containing capsaicin as the active ingredient. When applied to the skin of the affected area, pain and burning associated with the neuropathy are said to be reduced. However, capsaicin has been shown to kill nerve endings in some cases and is extremely irritating to the dermis. Thus this composition suffers from these disadvantages.

The use of ketamine transdermally in an organogel has shown some promise in the treatment of neuropathy. Ketamine is an N-methyl-D-aspartate receptor antagonist and thus blocks a cascade of intracellular events that inhibit the hyper excitability of spinal cord neurons. Animal data show that certain spontaneous pains and allodynia have been treated successfully with Ketamine. Also, in humans, phantom limb pain has been treated with success (Nadine & Bouhassira, Acta. Neurol. Scand 1999 (Supp 173):12-24). Ketamine has been used experimentally to treat neuropathic pain by a variety of routes including the intravenous and subcutaneous. The topical form of Ketamine is effective in treating painful neuropathy when other traditional medicines have failed. (Crowley et al., International Journal of Pharmaceutical Compounding 1998; 2:122-1273).

Other compositions have been employed, including combinations of individual compounds. U.S. Pat. No. 6,387,957 B1 (Frome) relates to the treatment of Sympathetically Mediated Pain (SMP), which include various neuropathies, employing the compounds ketamine (NMDA receptor antagonist), amitriptyline (anticholinergic antidepressant), and guanethidine (sympathetic blocking agent), in combination or independently. However, the compounds employed by Frome act independently of each other as illustrated by the effectiveness of individual compounds. Frome's invention lacks any synergism of the compounds as the compounds merely complement the other compounds, but does not synergize, or supplement, the activities of the other compounds. For example, ketamine a very potent antineuropathic agent was used in limited concentrations. Whether alone or in combination, small concentrations of ketamine were likely used due to ketamine's known neurotoxic effects. Frome's invention also suffers from limitations in the preparation, dosage, application or administration methods and potential side effects. The effectiveness of Frome's compounds depends on the volume of the preparation and whether the compounds are alone or in combination. The side effects of amitriptyline and guanethidine are well known. These are disruptive to a person's quality of life and are not addressed by Frome in his patent.

Accordingly, there remains a need in the art for effective treatments for neuropathies, and other neuropathic pains.

SUMMARY OF THE INVENTION

In a one aspect, the compositions described herein can provide for the treatment of peripheral neuropathy, and can include a therapeutically effective amount of ketamine, gabapentin and clonidine in a pharmaceutically acceptable diluent or carrier suitable for topical or transdermal use.

An additional ingredient can be added as needed to increase the analgesic effectiveness of the combination of ketamine, gabapentin, and clonidine. Specifically, topical compositions can include an additional ingredient that increases absorption and/or penetration of the combination of ketamine, gabapentin and clonidine.

The topical compositions described herein can also include an additional ingredient selected from the group consisting of: NMDA ligands, AMPA ligands, non-NMDA or AMPA ligands, TNF-1α ligand, GABA ligand and α-2 ligands. Additional ingredients can also be an analgesic.

In further embodiments, the additional ingredient can be selected from the group consisting of: capsaicin, lidocaine, bupivacaine, mepivacaine, ropivacaine, tetracaine, etidocaine, chloroprocaine, prilocalne, procaine, benzocaine, dibucaine, dyclonine hydrochloride, pramoxine hydrochloride, benzocaine, and proparacaine. The following can also be an additional ingredient: amitriptyline, baclofen, loperamide, nifedipine, pentoxifylline.

In an alternative embodiment of the compositions described herein, an analgesic which can potentiate the activity of ketamine could be admixed with ketamine and gabapentinin synergistic topical compositions. In one embodiment, the analgesic is clonidine. Suitable pharmaceutically acceptable carriers and/or diluents include conventional or unconventional solvents, dispersion media, fillers, aqueous solutions, antibacterial and anti-fungal agents, absorption-promoting agents, and the like.

Except insofar as any conventional medium or agent is incompatible with the active ingredients, use thereof in the pharmaceutical compositions described herein is contemplated. Supplementary active ingredients can also be incorporated into the compositions. For example, the topical composition may additionally include a Substance P blocking agent, a Mu-agonist, a non-NMDA calcium channel antagonist, or a TNF-1α antagonist.

The transdermal preparations described herein include any formulations suitable for topical application, and include: aqueous creams, ointments, gels, lotions, roll-on liquids, sprays, glass bead wound dressings, and synthetic polymer dressings impregnated with the compositions described herein. These preparations may also include compounds, such as dimethylsulfoxime, which would facilitate the passage of the active ingredients across the skin keratin barrier and into the epidermis. Preferably the preparation is a cream. Other formulations the compositions can be incorporated into include oils, suppositories, foams, liniments, aerosols, buccals, and sublingual tablets or transdermal devices for absorption through the skin or mucous membranes.

In other aspects, methods described herein are directed to treating peripheral neuropathy, comprising the step of transdermal or topical administration of an effective amount of a pharmaceutical composition of ketamine, gabapentin and clonidine to the affected area of a subject in need of such treatment. Other drugs or ingredients may be added as needed to increase the analgesic effect.

In preferred embodiments, the peripheral neuropathy is a diabetic neuropathy. It will be clearly understood that the diabetic neuropathy may be associated with Type 1 (insulin-dependent) diabetes, Type 2 (non-insulin-dependent) diabetes, or both.

In other preferred embodiments, the neuropathy is a non-diabetic neuropathy. Such a non-diabetic neuropathy may be genetically acquired, such as Charcot-Marie-Tooth syndrome. In other embodiments the peripheral neuropathy can result from a systemic or infectious disease such as HIV, or an infectious disease condition such as AIDS. In further embodiments, the peripheral neuropathy manifests as a post surgical complication.

In other embodiments the peripheral neuropathy is induced by a toxic agent. For example, the peripheral neuropathy can be caused by a chemotherapeutic agent such as taxol, vincristine, cisplatin, an agent used for the treatment of an infectious diseases such as streptomycin, didanosine or zalcitabine, or any other chemically toxic agent. Infectious disease conditions such as post-polio syndrome or AIDS-associated neuropathy are specifically contemplated.

Other peripheral neuropathies include the following: HIV associated neuropathy; $B_{12}$-deficiency associated neuropathy; cranial nerve palsies; drug-induced neuropathy; industrial neuropathy; lymphomatous neuropathy; myelomatous neuropathy; multi-focal motor neuropathy; chronic idiopathic sensory neuropathy; carcinomatous neuropathy; acute pan autonomic neuropathy; alcoholic neuropathy; compressive neuropathy; vasculitic/ischaemic neuropathy; mono- and poly-neuropathies.

In further embodiments, the neuropathy is due to low back pain, Guillain-Barre Syndrome, or sciatica.

Further embodiments include methods for treating a subject suffering from peripheral neuropathy, the methods comprising topically administering an effective amount of a composition comprising ketamine, gabapentin and a third analgesic which potentiates the activity of ketamine, formulated in a pharmaceutically acceptable topical carrier.

Other embodiments include methods for treating a subject suffering from neuropathic pains, the method comprising topically administering an effective amount of a composition comprising ketamine, gabapentin and clonidine, formulated in a pharmaceutically acceptable carrier for topical treatment.

The compositions described herein can be administered in therapeutically effective amounts. A therapeutically effective amount means the amount required to at least partly to attain the desired effect, i.e., to alleviate or prevent the symptoms of the peripheral neuropathy.

Such amounts will depend, of course, on the particular condition being treated, the severity of the condition, and individual patient parameters. These include age, physical condition, size, weight and other concurrent treatment. The amounts prescribed will be at the discretion of the attending physician. These factors are well known to those of ordinary skill in the art, and can be addressed with no more than routine experimentation. It is generally preferred that a minimum effective dose be determined according to sound medical judgment. It will be understood by those of ordinary skill in the art, however, that a higher dose may be administered for medical, psychological or other reasons.

The compositions described herein may be applied to the affected area of the skin of the patient. The frequency of application will depend on individual patient circumstances. For example, the compositions may be applied daily, twice daily, or even more frequently.

Methods and pharmaceutical carriers for preparation of pharmaceutical compositions, including compositions for topical administration are well known in the art, as set out in textbooks such as *Remington's Pharmaceutical Sciences*, 17th Edition, Mack Publishing Company, Easton, Pa., USA (updated in Gennaro, A. R., *Remington: The Science and Practice of Pharmacy*, $20^h$ edition, Lippincott, Williams & Wilkins) which is incorporated by reference in its entirety.

DETAILED DESCRIPTION

In one aspect, the pharmaceutical compositions described herein can be used for the treatment of peripheral neuropathy. These compositions can include a therapeutically effective amount of ketamine, gabapentin and clonidine in a pharmaceutically acceptable diluent or carrier suitable for transdermal or topical use. Preferably, the compositions comprise at least ketamine, gabapentin and clonidine, in amounts sufficient to potentiate an antineuropathic response when the compositions are administered transdermally in a physiologically acceptable transdermal vehicle.

As used herein "potentiated" or "synergistic" refers to an antineuropathic response or a pain-reducing response elicited through the synergistic effect of the compositions described herein, in which the combined effect of multiple agents is greater (in duration, intensity, comprehensively, or otherwise) than the sum of the effect produced by each agent alone. The vehicle can allow the active ingredients to efficiently penetrate tissues when applied topically and can allow increased concentrations of particular components (i.e., ketamine) and all added analgesic agents in the compositions described herein.

As used herein, "transdermal" or "percutaneous" delivery relates to delivery of a drug by passage into and through the skin or mucosal tissue. Hence the terms "transdermal", "topical" and "transmucosal" are used interchangeably unless specifically stated otherwise. Likewise the terms "skin," "derma," "epidermis," "mucosa," and the like shall also be used interchangeably unless specifically stated otherwise.

The compositions described herein may provide one or more of the following beneficial effects to a patient when topically applied in effective amounts: relief of pain, burning, tingling, electrical sensations and/or hyperalgesia. Also increased microcirculation, nitric oxide stabilization, and facilitated healing of skin ulcers and lesions. Additionally, protein kinase C inhibition, decreased oxidative stress, anti-inflammation, protection against radiation damage (particularly ultraviolet radiation), blockage of the formation of leukotrienes, stabilization of cell membranes, and/or promotion of the synthesis of nerve growth factor.

Ketamine is an N-methyl-D-aspartate (NMDA) calcium channel antagonist that can be admixed in the compositions described herein in concentrations ranging from 10-50%, preferably 10 to 30%, and most preferably from 15% to 20% safely. Topical ketamine is effective for treating painful neuropathy when other traditional medicines have failed. See Crowley K L, Flores J A, Hughes C N et al. "Clinical application of ketamine ointment in the treatment of sympathetically maintained pain", *International Journal of Pharmaceutical Compounding* 1998; 2:122-127.

Gabapentin is a glutamate antagonist at the NMDA and AMPA (sodium channel) receptor sites. This agent can be admixed in strengths ranging from 1 to 30 percent, but preferably in strengths less than 10%. The most preferred strength is 6%, but it can be reduced to 3% in case of pronounced ataxia. Because gabapentin is almost entirely eliminated by the renal route as unchanged drug, caution should be exercised with oral dosing (especially in renal-compromised patients.) More dosing flexibility is allowed transdermally because of its relatively low systemic concentration. Subsequent to the development of the compositions described herein, it was discovered that gabapentin also prevents ketamine neurotoxicity. See Bakonja M, Baydoun A, Edwards K R, et al. "Gabapentin for the symptomatic treatment of painful neuropathy in patients with diabetes mellitus—a randomized controlled trial." *JAMA* 1998; 280: 1831-1836. Also see Rowbatham M, Hardin N, Stacey B, et al. "Gabapentin for the treatment of postherpetic neuralgia—a randomized controlled trial." *JAMA* 1998; 280: 1837-1842. Subsequent to the discovery of the compositions described herein, it was discovered that gabapentin prevents neurotoxicity of certain compounds, see Farber, N B, et al. "Antiepileptic drugs and agents that inhibit voltage-gated sodium channels prevent NMDA antagonist neurotoxicity." *Mol Psychiatry* 2002; 7(7): 726-733.

Clonidine is an α-2 agonist that blocks norepinephrine release from sympathetic nerve endings. It also potentiates the action of ketamine. It can be admixed in strengths ranging from 0.001% to 2%, with the preferred strength ranging from 0.1 to 1%, the most preferred strength being 0.2%. See Hoffman B B, Lefkowitz R J. "Catecholamines, sympathomimetic drugs and adrenergic receptor antagonists" in *Goodman & Gilman's The Pharmacological Basis of Therapeutics*, ed. 10; New York, McGraw-Hill.

Without being bound to any particular theory of mechanism, the compositions described herein provide an antineuropathic response with a combination of drugs which synergistically or comprehensively affect multiple pathways associated with neuropathies, i.e., a synergistic "shotgun" effect. Again, without being bound to any particular theory of mechanism, it is proposed that the compositions described herein involves a double synergism. First, gabapentin is a glutamate antagonist; hence it's an effective analgesic. It also prevents the neurotoxicity of ketamine—a potent analgesic—thus allowing increased ketamine concentrations that will effect greater analgesia. Second, clonidine is an α-2 agonist acting against pain stimuli. It also potentiates the action of ketamine.

In an alternative embodiment of the compositions described herein, clonidine can be substituted with an alternative analgesic. Such analgesics contemplated by the compositions described herein potentiate the action of ketamine. The analgesics can be any known in the art, including, but not limited to NMDA ligands, AMPA ligands, non-NMDA or AMPA ligands, TNF-1α ligand, GABA ligand, α-2 ligands, and the like. Such analgesics can include clonidine, capsaicin, lidocaine, bupivacaine, mepivacaine, ropivacaine, tetracaine, etidocaine, chloroprocaine, prilocalne, procaine, benzocaine, dibucaine, dyclonine hydrochloride, pramoxine hydrochloride, benzocaine, and proparacaine. Those of skill in the art will readily recognize additional ingredients that can be admixed in the compositions described herein.

The topical pharmaceutical compositions described herein can further comprise alternative NMDA receptor antagonists, as an alternative to ketamine or as a supplemental analgesic. These antagonists can be competitive or non-competitive drugs. The NMDA receptor antagonist can be any known in the art, including, but not limited to dextromethorphan, dextrorphan, pyroloquinoline quinone, cis-4-(phosphonomethyl)-2-piperdine carboxylic acid, MK801, memantine, and their mixtures and pharmaceutically acceptable salts thereof.

In addition, the compositions described herein can further comprise additional ingredients which can increase the analgesic effectiveness of the combination of ketamine, gabapentin and clonidine. Such ingredients either facilitate the effect of this combination by increasing absorption and/or penetration, provide for a more comprehensive pain management regimen, or the like. Those of skill in the art will readily recognize additional ingredients that can be admixed in the compositions described herein. Preferably, the compositions described herein can comprise one or more of the following ingredients:

Amitriptyline 1% to 10%, Preferably 2% to 5% in Composition.

This tricyclic agent is a norepinephrine reuptake inhibitor. It can be used in strengths of 2% to 5%. See Goodkind K, Vrancken M A E, Feaster D. "On the putative efficacy of antidepressants in chronic, benign pain syndrome—an update." *Pain Forum* 1995; 4:237-247.

Baclofen 1% to 10%, Preferably 2% to 5% in Composition.

This drug is a $GABA_\beta$-agonist possessing presynaptic depressant action at NMDA and non-NMDA receptors. It can be used in strengths of 2% to 5%. See Evans R H, "The importance of NMDA receptors in the processing of spinal afferent input" in Collingridge G L, Watkins J C (Eds), *The NMDA Receptor* (2nd ed), New York, *Oxford University Press,* 1994; pp 266-276.

Capsaicin 0.001% to 0.1%, Preferably 0.025% in Composition.

This substance is a Substance P blocking agent currently used in a strength of 0.025%. It is a useful adjunct, but sometimes causes excessive skin irritation. The 0.025% strength is to prevent extreme dermal irritation). See Tandan R, Lewis G A, et al. "Topical capsaicin in painful diabetic neuropathy—a controlled study with long-term follow up" in *Diabetes Care* 1992; 15:8-14.

Loperamide 1% to 20%, Preferably 5% to 10% in Composition.

This anti-diarrheal agent is a Mu-agonist (similar to morphine, but without morphine's systemic side effects.) It can be added to the compositions described herein in strengths of 5% to 10%. See Nozaki-Taguchi N, Yaksh T L. "Characterization of the antihyperalgesic action of a novel peripheral mu-opioid receptor agonist—loperamide" in *Anesthesiology* 1999; 90:225-234.

Nifedipine 1% to 25%, Preferably 2% to 15% in Composition.

This drug is a non-NMDA calcium channel antagonist. It offers an additional protective effect with ketamine to block glutamate insult. This calcium channel blocker is especially useful for treating diabetic peripheral neuropathy. The agent can be added to the compositions described herein in strengths of 2% to 15% depending on the size of the treatment area. Due to circulatory and hypotension considerations, higher strengths may be used for areas below the waist (e.g., the feet) and lower strengths for areas above the waist. See Robertson S, et al. "The effects of the calcium antagonist nifedipine on peripheral nerve function in streptozotocin-diabetic rats" in *Diabetologia* 1992; 35:1113-1117.

Pentoxifylline 1% to 25%, Preferably 5% to 10% in Composition.

This vasodilator, a TNF-1α antagonist, is useful for low back pain. It can be added to the compositions described herein in strengths of 5% to 10%. See Yabuki S, et al. "Prevention of compartment syndrome in dorsal root ganglia caused by exposure to nucleus pulposus" in *Spine* 2001; 26:870-875.

The compositions described herein can further comprise components usually admixed in such preparations (besides ketamine, gabapentin and at least one additional analgesic, preferably clonidine). For example, the compositions may also include additional ingredients such as other carriers, moisturizers, oils, fats, waxes, surfactants, thickening agents, antioxidants, viscosity stabilizers, chelating agents, buffers, preservatives, perfumes, dyestuffs, lower alkanols, humectants, emollients, dispersants, sunscreens such as radiation blocking compounds or particularly UV-blockers, antibacterials, antifungals, disinfectants, vitamins, antibiotics, or other anti-acne agents, as well as other suitable materials that do not have a significant adverse effect on the activity of the topical composition. Additional ingredients for inclusion in the carrier are sodium acid phosphate moisturizer, witch hazel extract carrier, glycerin humectant, apricot kernel oil emollient, corn oil dispersant, and the like which are further detailed below. Those of skill in the art will readily recognize additional ingredients, which can be admixed in the compositions described herein.

The compositions described herein can be made by cold compounding. This is significant since one or more of the compounds admixed in the topical compositions described herein are sensitive to heat or other types of energy. Thus the activity of the composition may be detrimentally affected as a result of the formulation of the compositions in other manners. Hence, the ingredients of this topical composition are merely mixed together, without heating and using a sufficient amount of the carrier to provide a substantially homogeneous cream or ointment. It is generally preferred to dissolve, disperse or suspend one or more of the ingredients prior to cold compounding in order to ensure substantially homogeneous distribution of the active ingredients in the composition.

In addition to the foregoing components, the compositions described herein can optionally contain other ingredients. For example, triethanolamine can be added as a crosslinking agent. A preservative, such as betahydoxytoluene can also be added. Other irritation reducing agents can be added too. In this regard, irritation reducing agents can include, but are not limited to, glycerol. In some instances, semi-solid testosterone formulations have been prepared with propylene glycol and/or butylene glycol as the glycol component, ethyl alcohol and/or isopropyl alcohol as the alcohol component. Preservatives, a cross-linking agent, and additional irritation reducing agents can be included in formulations prepared in accordance with the methods described.

In other aspects, the methods described herein can include treating peripheral neuropathy, comprising the step of topical administration of a pharmaceutical composition of ketamine, gabapentin and clonidine (or alternative analgesic as described herein) to the affected area of a subject in need of such treatment. In preferred embodiments the methods described herein can provide a treatment of applying the compositions described herein to an affected area of a subject with diabetic polyneuropathy.

Other peripheral neuropathies include the following: HIV associated neuropathy; $B_{12}$-deficiency associated neuropathy; cranial nerve palsies; drug-induced neuropathy; industrial neuropathy; lymphomatous neuropathy; myelomatous neuropathy; multi-focal motor neuropathy; chronic idiopathic sensory neuropathy; carcinomatous neuropathy; acute pan autonomic neuropathy; alcoholic neuropathy; compressive neuropathy; vasculitic/ischaemic neuropathy; mono- and poly-neuropathies.

Thus, the methods and compositions described herein can be effective for neuropathies associated with systemic diseases such as: uremia; childhood cholestatic liver disease; chronic respiratory insufficiency; alcoholic polyneuropathy; multiple organ failure; sepsis; hypo-albuminemia; eosinophilia-myalgia syndrome; hepatitis; porphyria; hypo-glycemia; vitamin deficiency; chronic liver disease; primary biliary cirrhosis; hyperlipidemia; leprosy; Lyme disease; herpes zoster; Guillain-Barre syndrome; chronic inflammatory demyelinating polyradiculoneuropathy; sensory perineuritis; acquired immunodeficiency syndrome (AIDS)—associated neuropathy; Sjogren's syndrome; primary vasculitis (such as polyarteritis nodosa); allergic granulomatous angiitis; hypersensitivity angiitis; Wegener's granulomatosis; rheumatoid arthritis; systemic lupus erythematosis; mixed connective tissue disease; scleroderma; sarcoidosis; vasculitis; systemic vasculitides; acute tunnel syndrome; pandysautonomia; primary, secondary, localized or familial systemic amyloidosis; hypothyroidism; chronic obstructive pulmonary disease; acromegaly; malabsorption (sprue, celiac disease); carcinomas (sensory, sensorimotor, late and demyelinating); lymphoma (including Hodgkin's), polycythemia vera; multiple myeloma (lytic type, osteosclerotic, or solitary plasmacytoma); benign monoclonal gammopathy; macroglobulinemia; cryoglobulinemia; tropical myeloneuropathies; herpes simplex infection; cytomegalovirus infection; and diabetes.

Genetically acquired neuropathies suitable for treatment by the methods and compositions described herein include, without limitation: peroneal muscular atrophy (Charcot-Marie-Tooth Disease) hereditary amyloid neuropathies, hereditary sensory neuropathy (type I and type II), porphyric neuropathy, hereditary liability to pressure palsy, Fabry's Disease, adrenomyeloneuropathy, Riley-Day Syndrome, Dejerine-Sottas neuropathy (hereditary motor-sensory neuropathy-III), Refsum's disease, ataxia-telangiectasia, hereditary tyrosinemia, anaphalipoproteinemia, abetalipoproteinemia, giant axonal neuropathy, metachromatic leukodystrophy, globoid cell leukodystrophy, and Friedrich's ataxia.

In alternative embodiments compositions described herein are directed to treatment of neuropathic pain, especially pain caused by nerve injury or sympathetically mediated pain. Sympathetically mediated pain (SMP) is a type of pain in which over activity of the sympathetic nervous system plays a crucial role. It includes the syndromes of reflex sympathetic dystrophy, causalgia, neuropathic pain secondary to nerve injury, and pain from neuromas. It encompasses all neurogenic pain that is not central and is related to a nerve injury regardless of the cause. Neuropathic pain syndromes include, without limitation (other than the neuropathies described herein), allodynia, various neuralgias such as post herpetic neuralgia and trigeminal neuralgia, phantom limb pain, hyperpathia, hyperesthesia, hyperalgesia, dyesthesia, paresthesia, anesthesia delorosa, deafferentation pain, and complex regional pain syndromes, such as reflex sympathetic dystrophy and causalgia. Specific examples include low back pain, sciatica, Guillain-Barre Syndrome, post-surgical traumatic neuropathy, and diabetic peripheral polyneuropathy.

Methods described herein can also involve the topical application of a composition described herein to areas of the skin in the vicinity of tissue that suffers from the neuropathic pain. In particular, the compositions and methods described herein are useful on the patients' extremities such as the peripheral appendages (e.g., fingers, toes, hands and feet) and general areas of pain (e.g., back, shoulder, neck) where the neuropathic pain, particularly peripheral neuropathy, is often the most pervasive. The methods and compositions described herein can also applied to the specific ganglia that mediate pain to the spinal column and to the spine itself. Specific dermatomes are involved for the correct application of the compositions described herein for neuropathic analgesia.

For example, a suitable amount of a composition described herein can be applied one to six times daily as needed to relieve pain and other symptoms of diabetic polyneuropathy. Preferably, the composition is applied two to four times daily, as needed for pain. A sufficient amount is applied to cover the area afflicted by the diabetic polyneuropathy with a thin layer of the composition and the composition is rubbed into the skin until little or no residue remains on the skin. Treatment begins initially to treat acute symptoms but may be continued indefinitely to relieve pain, prevent symptoms of diabetic polyneuropathy from returning and possibly restore some nerve and/or skin function. The application frequency and volume of the composition may decrease over time, but not necessarily.

The methods described herein may also provide one or more of the beneficial effects described above for the compositions described herein. In addition, methods described herein can provide some additional beneficial effects due to one or more of the ingredients contained in the pharmaceutically acceptable carrier such as described above, e.g., the return of sensory perception at the application site.

The methods described herein also encompass topical administration of compositions in a physiologically acceptable transdermal vehicle and in an amount and duration sufficient to provide an antineuropathic response. Administration to the subject is performed in accordance with that mode which is most amenable to the topically acceptable form chosen. For example, gels, lotions, creams, and ointments are preferably administered by spreading. Because hydrated skin is more permeable than dry skin, the dosage form can be modified or an occlusive dressing can be applied to facilitate absorption. Also contemplated by the compositions and methods described herein are slow-release or sustained-release forms, whereby a relatively consistent level of the composition, particularly ketamine, gabapentin and at least one additional analgesic are provided over an extended period.

A subject can be treated in accordance with the compositions described herein by administering the composition suspended in or admixed with a physiologically suitable transdermal vehicle and manually applied or sprayed (either with a manually-actuated pump or with the aid of a suitable pharmaceutically-acceptable propellant) onto the surface area in need of treatment. Preferably, the composition is applied by topical massage. Suitable formulations for topical application of drugs are well known to those of ordinary skill in the art and can be routinely selected.

The amount of composition to be applied varies on the choice of vehicle as well. For example, when the composition is administered by spraying an alcoholic liquid solution of the drug, the total volume in a single dose can be very low. Conversely, when the compositions described herein are administered in a transdermal cream, the total volume can be higher. The vehicle selected and its manner of application is preferably chosen in consideration of the needs of the patient and the preferences of the administering medical practitioner.

The general mode of action of the compositions described herein is through "transdermal administration." This mode of action is restricted to the region below the surface of the dermis where the drug application has occurred. In using the transdermal route of administration, the amount of composition absorbed systemically is minimal. This is especially true when the application site(s) is/are below the beltline. Transdermal administration of the compositions described herein is directed to cutaneous surfaces. The composition can be applied transdermally on a subject in an amount and duration sufficient to prevent or relieve pain associated with any cause, including, but not limited to, neuropathic inflammation, and acute and chronic peripheral neuropathy.

Transdermal application of the compositions described herein is useful for relieving pain, inflammation and irritation associated with skin diseases and disorders. Painful lesions develop, for example, from viral infections, i.e., herpes zoster, skin cancers and genetic disorders. Acute post-operative or surgical pain can be reduced or even eliminated as can pain associated with chronic disorders, such as diabetic peripheral polyneuropathy.

The formulations in which the compositions described herein are incorporated can assume any of a variety of dosage forms, including solutions, suspensions, ointments, and solid inserts. Examples are creams, lotions, gels, ointments, suppositories, sprays, foams, liniments, aerosols, buccal and sublingual tablets, various passive and active transdermal devices for absorption through the skin and mucous membranes, and the like.

Typical pharmaceutically acceptable carriers are, for example, water, mixtures of water and water-miscible solvents such as lower alkanols or vegetable oils, and water-soluble ophthalmologically acceptable non-toxic polymers, for example, cellulose derivatives such as methylcellulose. A typical cream or ointment-type carrier for topical application that can be used according to the methods and compositions described herein include a mixture of water, glycerin, propylene glycol, and methylparaben. Topical carriers may also include other conventional emulsifiers and emollients including alginates, glyceryl stearate, PEG-100 stearate, cetyl alcohol, propylparaben, butylparaben, sorbitols, polyethoxylated anhydrosorbitol monostearate (TWEEN), white petrolatum (VASELINE), triethanolamine, Emu oil, aloe vera extract, lanolin, cocoa butter, and the like. Suitable topical carriers are well known to the skilled artisan. Standard texts, such as Gennaro, A. R., *Remington: The Science and Practice of Pharmacy*, $20^h$ edition, Lippincott, Williams & Wilkins; Hardman, J. G., *Goodman & Gilman's The Pharmacological Basis of Therapeutics*, $10^{th}$ edition, McGraw-Hill Professional; Shah & Maibach, *Topical Drug Bioavailability, Bioequivalence, and Penetration*, 1st edition, Plenum Pub Corp.; Hillery et al., *Drug Delivery and Targeting: For Pharmacists and Pharmaceutical Scientists*, Harwood Academic Pub.; Ansel et al., *Pharmaceutical Dosage Forms and Drug Delivery Systems*, 7th edition, Lippincott Williams & Wilkins (each incorporated herein by reference), can be consulted to prepare suitable compositions for topical administration, without undue experimentation. Suitable dosages can also be determined based upon the text and documents cited herein. Characteristics which determine preferred carriers include ease of application, hypoallergenicity, the ability to contain a minimum of 30% of its weight in active drugs, aesthetically pleasant, and the ability to permeate/penetrate the skin.

Preferably, Lipoderm® (Professional Compounding Centers of America, Houston, Tex.) is admixed in the compositions described herein. Alternative ointment bases are known to persons skilled in the art. Sufficient Lipoderm® base is admixed to act as a carrier for the active ingredients of the composition. Typically the Lipoderm® base will make up more than about 70% of the total composition and more preferably about 74% of the composition is the Lipoderm® base. The Lipoderm® base functions as a carrier and enhances penetration into the skin. It is also hypoallergenic and is aesthetically pleasing.

A typical transdermal gel base, provided herein for exemplary purposes only, can contain lecithin, isopropyl palmitate, poloxamer 407, and water. Topical carriers with different viscosities and hand-feel are known to the art. The above active ingredients can be dispersed within the pharmaceutically acceptable carrier in therapeutically effective amounts to treat neuropathies, and the other maladies described above. Preferably, the topical pharmaceuticals described herein contain (per gram total weight) from about 15 grams per 100 gram weight of ketamine, from about 6 grams per 100 grams weight of gabapentin, and from about 0.2 grams per 100 grams weight of clonidine. Other analgesic agents can be added accordingly, e.g., capsaicin.

Transdermal dosage unit forms can be prepared utilizing a variety of techniques that have been described in the art. For example, in U.S. Pat. Nos. 4,861,800; 4,868,218; 5,128,145; 5,190,763; and 5,242,950; and in the foreign patent documents EP-A 404807; EP-A 509761; and EP-A 593807. (each of which is incorporated by reference in its entirety). A monolithic patch structure can be utilized in which selegiline is directly incorporated into the adhesive and this mixture is cast on to a backing sheet. Alternatively, selegiline as an acid addition salt can be incorporated into a multi layer patch which effects a conversion of the salt to selegiline-free base, as described for example in EP-A 593807. One can also employ a device using a lyotropic liquid crystalline composition in which, for example, 5-15% of selegiline is combined with a mixture of liquid and sold polyethylene glycols, a polymer, and a non-ionic surfactant, optionally with the addition of propylene glycol and an emulsifying agent. For further details on the preparation of such transdermal formulations, reference can be made to EP-A 509761.

"Drug delivery system," "drug/enhancer composition," or any similar terminology relates to a formulated composition containing the drug to be transdermally delivered in combination with a penetration enhancer. Other pharmaceutically acceptable materials or additives can also be contained in the drug/enhancer composition, such as a diluent, skin-irritation reducing agent, carrier or vehicle, excipient, plasticizer, emollient, or other additive and mixtures thereof provided that such additives do not materially affect the basic and novel characteristics of the matrix patch.

The terms "matrix," "matrix system," or "matrix patch" relate to an active permeant or drug dissolved or suspended in a biocompatible polymeric phase, preferably a pressure sensitive adhesive, that can also contain other ingredients or in which the enhancer is also dissolved or suspended. This definition is meant to include embodiments wherein such polymeric phase is laminated to a pressure sensitive adhesive or used with an overlay adhesive. A matrix system usually and preferably comprises an adhesive layer having an impermeable film backing laminated onto the distal surface thereof and, before transdermal application, a release liner on the proximal surface of the adhesive. The film backing protects the polymeric phase of the matrix patch and prevents release of the drug and/or enhancer to the environment. The release liner functions similarly to the impermeable backing, but is removed from the matrix patch prior to application of the patch to an application situs. Matrix patches are known in the art of transdermal drug delivery to routinely contain such backing and release liner components, and matrix patches according to the compositions described herein should be considered to comprise such backing and release liner or their functional equivalents. U.S. Pat. No. 5,122,383 (incorporated herein by reference) describes such backing and release liner. A matrix system therefore relates to a unit dosage form of a drug composition in a polymeric carrier, also containing the enhancer and other components that are formulated for maintaining the drug composition in the polymeric layer in a drug transferring relationship with the derma, i.e. the skin or mucosa. A matrix patch is distinguished from a "liquid reservoir patch," wherein an active permeant or drug is dissolved in a gelled liquid contained in an occlusive device having an impermeable back surface and an opposite surface configured appropriately with a permeable membrane and adhesive for transdermal application, e.g., U.S. Pat. No. 4,983,395, incorporated herein by reference in its entirety.

A typical transdermal formulation comprises a conventional aqueous or non-aqueous vehicle, for example, a cream, ointment lotion or paste or in the form of a medicated plaster, patch or membrane.

The pharmaceutical preparation may also contain non-toxic auxiliary substances such as emulsifying, preserving, wetting, and bodying agents, as for example, polyethylene glycols; antibacterial components such as quaternary ammonium compounds; buffering ingredients such as alkali metal chloride; antioxidants such as sodium metabisulfite; and other conventional ingredients such as sorbitan monolaurate.

The term "effective amount" of a drug or permeant relates to a nontoxic but sufficient amount of a compound to provide the desired local or systemic effect without adverse side effects. An "effective amount" of permeation enhancer as used herein relates to an amount selected so as to provide the desired increase in membrane permeability and, correspondingly, the desired depth of penetration, rate of administration, and amount of drug.

As used herein, "application situs" relates to a site suitable for topical application with or without the means of a device, patch, or dressing, e.g. the spinal column, behind the ear, on the arm, back, chest, abdomen, leg, top of foot, etc.

The penetration enhancing compositions of the compositions described herein may constitute a small amount of the formulation or a large amount depending on which transdermal vehicle is used, which systemically and/or topically active agent is used, and the type of biological effect sought. The amount will be readily apparent to those skilled in the art, since the total amount of penetration enhancers will be approximately the same as those of the prior art. For example, when the potency of the penetration enhancement composition is greatly increased, lower quantities can be used.

Subjects to whom the formulations can be administered are primarily mammals, including humans, pets, and livestock and other farm animals and sport animals. The compositions and methods described herein are preferably used on humans. The term "topical administration" or "topical application" refers to directly layering or spreading upon epidermal tissue, especially outer skin or membrane, including the skin or membrane of the oral or vaginal cavities.

The site of application is dependent on many factors including, but not limited to, the amount of drug to be delivered, the extent of enhancement required, the side effects manifested and the time of application. Thus, another important facet of the methods described herein is the use of these compositions with drugs other than for example, testosterone, or to apply such formulations, or topical products in general, specifically to the soles of the feet, the palms of the hands or other immune-privileged sites of the body. Also, the drugs, compositions or products may be administered later in the day or at night when the permeability at the site of application is higher.

The amount of composition necessary to produce a therapeutic effect at an affected area is based on various factors, including the strength of the active ingredients, the ingredients admixed, the pain type and intensity, or related to, the location and size of the area and the relative condition that is to be treated. For example, the amount of composition needed to treat severe pain is likely to be greater than the amount of composition needed to treat mild to moderate forms of the affliction. In addition, an acute condition will likely require less medication for less time than a chronic condition. Individual sensitivities will also influence the dosage amounts administered to a particular subject. A determination of the appropriate dose is within the skill of one in the art given the parameters herein. In terms of the compositions described herein, the preferred dosage range is preferably determined by considering the amount of ketamine, gabapentin and at least one additional analgesic delivered, in percentage, and the surface area to be treated. The concentration of the active ingredients, in the pharmaceutical composition can be from about 0.001% to about 50% ketamine, about 0.001% to about 50% gabapentin, 0.001% to about 2% clonidine, and about 0.001% to about 0.1% capsaicin. In accordance with the compositions and methods described herein, the foregoing doses can be readily optimized following the teachings herein, based on known pharmacological protocol, by those of ordinary skill in the art, with no more than routine optimization. Of course, the preferred lower limit for drug delivery is that necessary to bring about an anti-neuropathic effect. The preferred upper limit is less than that amount which produces untoward side effects.

Although not crucial, the dilution and/or formulation of the active ingredients of the compositions described herein, in a physiologically acceptable transdermal vehicle, can be important and useful in providing the final dosage concentration. The compositions can be supplied in solid, semi-solid or liquid forms, including tablets, capsules, powders, liquids, and suspensions. The compositions described herein can therefore encompass concentrated forms for subsequent dilution before use or sale. The compositions can comprise any physiologically acceptable topical excipients including, but not limited to, gels, lotions, creams, ointments, and liquids.

EXAMPLES

The active ingredients of the compositions described herein are composed of three chemicals within a transdermal base. The chemicals are (1) ketamine, an N-methyl-D-aspartate (NMDA) calcium channel antagonist. It can be used safely in preferable concentrations of 15% or 20% when combined with gabapentin. (2) Gabapentin, a glutamate antagonist at the NMDA and AMPA (sodium channel) receptor sites. Its concentration is typically 6%, but can be reduced to 3% or less for gabapentin-sensitive patients. Gabapentin also prevents ketamine neurotoxicity. (3) Clonidine, an α-2 agonist that blocks nor-epinephrine release from sympathetic nerve endings. It also potentiates the action of ketamine. Its concentration in the formula is 0.2%, but can be further reduced or eliminated for clonidine-allergic patients. Eliminating clonidine, however, will result in a less-than-optimal analgesic compound. The transdermal vehicle Lipoderm® is used. It has the exceptional ability to contain up to 50% of its weight in active drugs. It is also cosmetically elegant and has a hypoallergenic compatibility with human dermis. The combination of the 3 agents within the Lipoderm® base act synergistically to relieve neuropathic pain.

Side effects are possible with the compositions described herein, especially drowsiness and/or dizziness. For example, Gabapentin is known to cause ataxia when taken orally as an oral capsule or tablet. Clonidine is a potent hypotensive agent, and hence, at times can markedly reduce blood pressure. Transdermal application usually prevents these potential side effects. Follow-up surveys have proven this.

One preferred method of preparation is as follows. Clonidine was triturated to a fine powder. Clonidine, ketamine, and gabapentin powders were filtered through a fine-mesh screen into the appropriate vessel (e.g., a glass mortar.) Powders were wetted with sufficient propylene glycol. Some Lipoderm® was added to suspend the wet powders. The remainder of Lipoderm® was added and triturated till mixed. Krisgel® 1% (of the total compound) was added to thicken. An ointment mill was used to completely mix and smooth the cream. The resulting cream looked and felt like custard.

Administration

The compositions described herein may be applied two ways via massage: (1) directly to the pain site or appropriate ganglion and (2) into the appropriate dermatome on the spine.

Plan 1 is normally used first, especially if the pain locus is below the belt (due to reduced systemic circulation of the agents.) The patient is instructed to find the most precise area of pain—if possible—by using a blunt, pointed object (i.e., fingertip, pen tip, etc.) By use of a "checkerboard pattern" search, many times the pain locus is discovered. For example, a foot pain locus may be found by pressing a fingertip on one side of the ankle for approximately 2 seconds then moving the fingertip an inch towards the other side of the ankle. This pressure is repeated "checkerboard style" (across and downward) until the entire foot—top and bottom—has been covered. The patient takes note of what area(s) hurt most and then treats the area(s) with ½ gram or 1 gram of cream at each pain site. If a precise locus cannot be found, then a 1 gram dose to the nerve bundle located ¾ inch below and ¾ inch behind the inside anklebone will suffice. This nerve bundle is responsible for innervation of the foot via the L-4, L-5, S-1, and S-2 dermatomes. Other ganglia may be used similarly for pain loci at other anatomical sites. An anesthesiologist—or a medical professional with a thorough understanding of human anatomy—should be consulted for the most appropriate ganglion (or ganglia) to be used.

Plan 2 is used when there is insufficient analgesia provided by Plan 1. Plan 2 requires massage of the cream into the appropriate dermatome on the spinal column. The patient is shown where the correct dermatome application site (on the spine) is for the painful area described by the patient. For example, a foot pain locus requires cream application to the L-4, L-5, S-1, and S-2 vertebrae on the spine.

How much cream to apply depends on (1) the pain site and (2) pain severity. The patient is instructed to use Plan 1 first. During the counseling session, the patient learns to (1) find the pain using the "checkerboard technique" described above and (2) prepare the skin for application by warming the site with a very warm, slightly moist cloth. A minimum dose—usually between ½ to 1 gram—is suggested as a starting dose. A (1-gram+½ gram) dosing spoon is given to the patient for accurate measure. The patient is instructed to use this starting dose 3 times daily for 3 days unless side effects appear. If that happens, the patient is counseled to immediately cease the applications and call his/her doctor. After the 3 day period—and if no sign of analgesia nor side effects—the dose may be increased by ½ gram increments daily. For example, if a 1-gram dose to the site did not relieve the pain during the first 3 days, then the dose would be increased by ½ gram per application on day 4. If the pain was still not managed, the dose would be increased by another ½ gram dose on day 5. The dose total at that point would be 2 grams per application. This sequence would be repeated until (1) the pain is managed or (2) side effects begin. Note: Side effects at any time are the limiting factor for dosing.

If Plan 1 does not provide sufficient analgesia within 7 days of the first application, then the patient is instructed to initiate Plan 2. Application to this area is explained above. Because the area is above the belt line, the patient is told that there is an increased risk of side effects. A 1-gram dose at the correct dermatome is started with the proviso that the dose may be adjusted down or up after a 3 day dosing period. This is similar to Plan 1.

Dosing frequency is dependent on the cream's duration of action. Duration of action varies from patient to patient. Normally, the cream is applied 3 times daily, but more frequent— or less frequent—applications are possible. Again, the limiting factor is side effects. Hence, if no side effects, then multiple daily applications are OK. The cream is a pain management "tool". As such, the cream may be used as often as necessary (subject to side effects.)

Objectives and Advantages

Pain management is one objective of the compositions and methods described herein. The methods and compositions described herein can ameliorate neuropathic pain in patients. The compositions and methods described herein have the following advantages: (1) Surveys have shown that >75% of patients using the compositions described herein have managed their neuropathic pain with at least one embodiment described herein; (2) the compositions described herein are effective against a wide variety of sympathetically mediated pain (SMP) sources—including various neuropathies, low back pain, sciatica, and post-spinal surgery pain; (3) the doses needed to control neuropathic pain are relatively small (see survey, Table 1); (4) dose volumes are also small—a distinct application advantage; (5) patients affected by side effects total less than 22% (includes those who "failed" the cream); (6) the compositions described herein are cosmetically elegant; (7) the compositions described herein are easy to apply because they are readily absorbed by the prepared skin.

that about 50% of patients were experiencing sufficient analgesia. Subsequently, the Ketamine amounts were increased and then capsaicin was added to the basic formula.

Compound #2 achieved a pain reduction of 4 points=a 51% pain reduction. Note that the baseline pain level is 0.6 points higher than for the 10% gel. Also, more people (#87) have used the 15% strength of the compositions described herein than any other formulation. There were 21 reported failures. The 66 patients who successfully used this 15% combination (a success rate of 76%) represent a statistically significant sample.

Compound #3 also achieved a pain reduction of 4 points, and this=a 50% pain reduction. The baseline pain level was 0.1 point higher than the 15% compound, but the increased analgesia expected due to the addition of Capsaicin did not materialize statistically. The small sample size—9 patients with 1 failure—is probably responsible. But since there was a success rate of 89%, this combination is worth keeping. This embodiment has now been replaced by ketamine 20% plus Capsaicin 0.025%, which was shown to be much more effective. It is used when there is some—but insufficient—analgesia achieved with differing embodiments of the compositions described herein. See description of Compound #4 (below) for further discussion.

Compound #4 scored best, based on the illustrated statistics. With a pain reduction of 4.3 points from a baseline pain level of 8.3, pain reduction averaged 52% for the 17 patients who responded to the survey. The success rate of 85% is noteworthy (17 favorable responses and 3 failures). As noted

TABLE 1

| I. Number of Patients | Compound Components | Initial Pain Level (10-point scale) | Amount Applied | Application Frequency (Times/day) | Pain Level: One Week | Duration of Action |
|---|---|---|---|---|---|---|
| 8 | Ketamine 10% + Gabapentin 6% + Clonidine 0.2% in a Pluronic-Lecithin-Organogel Transdermal Vehicle | 7.3 | 1.4 grams | 1.8/day | 3.0 | 5.1 hours |
| 66 | Ketamine 15% + Gabapentin 6% + Clonidine 0.2% in PLO or Lipoderm ® Transdermal Vehicle | 7.9 | 1.5 grams | 1.9/day | 3.9 | 7.9 hours |
| 8 | Ketamine 15% + Gabapentin 6% + Clonidine 0.2% + Capsaicin 0.025% in PLO or Lipoderm ® | 8.0 | 1.5 grams | 2.1/day | 4.0 | 5.5 hours |
| 17 | Ketamine 20% + Gabapentin 6% + Clonidine 0.2% in PLO or Lipoderm ® Transdermal Vehicle | 8.3 | 1.9 grams | 2.2/day | 4.0 | 4.4 hours |

Table 1 above describes the most commonly used varieties of the compositions described herein. A subjective 10-point pain scale was used by the patients at baseline and at 7 days to describe their pain. A "1" essentially meant no pain. A "10" described very severe pain—the kind that leaves one in agony. The amount applied was judged by the number of 1 gram—½ gram dispensing spoons used per application. There was tremendous Application Frequency variability. Application times ranged from every other day to 5 times daily.

Onset of analgesia for all four composition varieties share the same time period. These times varied from a half hour to over 72 hours. For reasons not known, the onset times differed from patient to patient.

Compound #1 achieved a pain reduction of 4.3 points=59% pain reduction. In the survey, 14 people used the 10% strength PLO-based (pluronic-lecithin organogel) transdermal gel but 6 reported treatment failure. This represents a success rate of 57%. But the 14 patients who used this gel represent a statistically small sample. It was noticed early on in paragraph 3, the 20% Ketamine combination with Capsaicin added should prove to be the best.

All publications and patent documents cited in this specification are herein incorporated by reference as if each individual publication or patent application were specifically and individually indicated to be incorporated by reference.

Although the foregoing methods and compositions have been described in some detail by way of illustration and example for purposes of clarity of understanding, it will be readily apparent to those of ordinary skill in the art in light of the teachings of these methods and compositions that certain changes and modifications may be made thereto without departing from the spirit or scope of the appended claims.

What is claimed is:

1. A method for treating a subject suffering from peripheral neuropathy, said method comprising topically administering to the subject an effective amount of a composition comprising ketamine, gabapentin and a third analgesic which potentiates the activity of ketamine, formulated in a pharmaceutically acceptable topical carrier.

2. The method of claim 1, wherein the composition comprises ketamine in an amount of greater than 10% by weight.

3. A method for treating a subject suffering from neuropathic pains, said method comprising topically administering to the subject an effective amount of a composition comprising ketamine, gabapentin and clonidine, formulated in a pharmaceutically acceptable carrier for topical treatment.

4. The method of claim 3, wherein the composition comprises ketamine in an amount of greater than 10% by weight.

5. A method for treating a subject suffering from peripheral neuropathy, comprising:
topically administering to the subject an effective amount of a composition comprising 1) ketamine in an amount of greater than 10% by weight, 2) gabapentin and 3) a third compound which potentiates the activity of the ketamine.

6. The method of claim 5, wherein the peripheral neuropathy is genetically acquired.

7. The method of claim 5, wherein the peripheral neuropathy results from a systemic or infectious disease.

8. The method of claim 5, wherein the peripheral neuropathy is diabetic neuropathy or Guillain-Barre Syndrome.

9. The method of claim 5, wherein the peripheral neuropathy is induced by a toxic agent.

10. The method of claim 5, wherein the peripheral neuropathy manifests as a post-surgical complication.

11. The method of claim 5, wherein the peripheral neuropathy is low back pain.

12. The method of claim 5, wherein the peripheral neuropathy is sciatica, a cancer-induced neuropathy, cancer-related neuropathy or sympathetically mediated pain.

13. The method of claim 5, comprising topically administering to a subject an effective amount of a composition comprising ketamine in an amount of greater than 15% by weight.

14. The method of claim 5, wherein the third compound comprises clonidine.

15. The method of claim 5, wherein the composition comprises gabapentin in an amount of less than 10% by weight.

16. The method of claim 5, wherein the third compound is selected from an NMDA ligands, AMPA ligands, non-NMDA or AMPA ligands, TNF-1α ligand, GABA ligand and α-2 ligands.

17. The method of claim 5, wherein the third compound is selected from an Substance P blocking agent, a Mu-agonist, a non-NMDA calcium channel antagonist, or a TNF-1α antagonist.

18. The method of claim 5, wherein the composition is applied directly to the site of the pain, to the ganglia mediating the pain, or to the spinal column.

19. The method of claim 5, wherein said composition is incorporated into a formulation selected from the group consisting of: cream, lotion, gel, oil, ointment, suppository, spray, foam, liniment, aerosol, buccal and sublingual tablet or a transdermal device for absorption through the skin or mucous membranes.

20. The method of claim 5, wherein the composition is administered repeatedly to the subject.

* * * * *